United States Patent [19]
Clarke

[11] Patent Number: 6,110,989
[45] Date of Patent: Aug. 29, 2000

[54] DENTURE ADHESIVE

[75] Inventor: Hal C. Clarke, Woodbridge, N.J.

[73] Assignee: Block Drug Company, Inc., Jersey City, N.J.

[21] Appl. No.: 09/407,649

[22] Filed: Sep. 28, 1999

Related U.S. Application Data

[63] Continuation-in-part of application No. 09/163,698, Sep. 30, 1998, abandoned.

[51] Int. Cl.$^7$ ..................................................... A61K 6/00
[52] U.S. Cl. ............................................................ 523/120
[58] Field of Search .............................................. 523/120

[56] References Cited

U.S. PATENT DOCUMENTS

| | | |
|---|---|---|
| 3,003,988 | 10/1961 | Germann et al. . |
| 4,071,669 | 1/1978 | Chang et al. ........................... 526/47.3 |
| 4,373,036 | 2/1983 | Chang et al. . |
| 4,514,528 | 4/1985 | Dhabhar . |
| 4,521,551 | 6/1985 | Chang et al. . |
| 4,542,168 | 9/1985 | Chang et al. . |
| 4,569,955 | 2/1986 | Dhabhar . |
| 4,910,247 | 3/1990 | Haldar et al. . |
| 4,929,690 | 5/1990 | Goertz et al. . |
| 4,952,634 | 8/1990 | Grossman et al. ....................... 525/190 |
| 4,980,391 | 12/1990 | Kumar et al. . |
| 5,006,571 | 4/1991 | Kumar et al. . |
| 5,073,604 | 12/1991 | Holeva et al. . |
| 5,093,387 | 3/1992 | Schobel et al. . |
| 5,104,926 | 4/1992 | Russell et al. . |
| 5,204,414 | 4/1993 | Pelah et al. . |
| 5,279,378 | 1/1994 | Mateeck et al. ........................ 524/501 |
| 5,298,534 | 3/1994 | Prosise et al. . |
| 5,395,867 | 3/1995 | Prosise . |
| 5,424,058 | 6/1995 | Rajaiah et al. . |
| 5,525,652 | 6/1996 | Clarke et al. . |
| 5,750,591 | 5/1998 | Clarke et al. ........................... 523/120 |
| 5,753,723 | 5/1998 | Chang et al. ........................... 523/120 |
| 5,763,554 | 6/1998 | Prosise .................................... 526/271 |
| 5,776,362 | 7/1998 | Sato et al. ............................... 252/194 |
| 5,872,161 | 2/1999 | Liang et al. ............................ 523/120 |
| 5,877,233 | 3/1999 | Liang et al. ............................ 523/120 |

FOREIGN PATENT DOCUMENTS

| | | |
|---|---|---|
| WO 92/10988 | 7/1992 | WIPO . |
| WO 95/33435 | 12/1995 | WIPO . |

*Primary Examiner*—Paul R. Michl

[57] ABSTRACT

A denture adhesive comprising a partial, mixed salt of a copolymer of an alkyl vinyl ether and maleic acid copolymer produced by a wet process, wherein the cations of said salt comprise i) calcium with a degree of substitution of the copolymer in calcium of at least about 69%; and ii) at least one other cation selected from the group consisting of sodium and potassium.

12 Claims, No Drawings

DENTURE ADHESIVE

This patent application is a continuation-in-part of prior patent Application No. 09/163,698 filed Sep. 30, 1998, abandoned.

BACKGROUND OF THE INVENTION

1. Field of the Invention

The invention relates to denture adhesives and methods for making denture adhesives.

2. Description of Related Art

Dentures are substitutes for missing teeth and serve as replacement for all or some of the teeth found in the oral cavity. Despite diligent efforts by dental professionals and designers of dental prostheses, dentures do not always fit perfectly. Over time, even well-fitting dentures can become ill-fitting due to natural shrinkage and changes in the gum or mucous tissues. Therefore, adherent creams, liquids or powders are often used to secure or temporarily fix dentures within the mouth.

There are a number of desirable attributes of a denture adhesive composition. The denture adhesive should develop a high degree of tack upon contact with saliva so that the dentures can be held in place as soon as they are seated in the mouth. It is also highly desirable that the mucilage of the fixative be spread over the denture-mucosa interface in order to seal the denture in place effectively. The mucilage should possess sufficient cohesive strength to withstand the stresses of mastication, which act to rupture the seal and thus dislodge the denture. The denture adhesive must also exhibit sufficient resistance to degradation under the extreme environmental changes that can occur in the oral cavity during such common actions as drinking hot or cold beverages. Of course, the adhesive must also be releasable so that the denture wearer may remove the dentures for cleaning and maintenance. Denture adhesives are generally sold as a cream, liner or strip, liquid or powder, and many examples are well known in the art.

Early denture adhesives contained finely ground particles of natural gums that expanded when wet with water to become a viscous gel, which acted as a cushion and an adherent between the denture plate and the gum tissue. These denture adhesives, however, have been largely supplanted by polymeric denture adhesives in recent years.

U.S. Pat. No. 3,003,988 to Germann discloses a mixed partial salt of a methyl vinyl ether/maleic acid (or maleic anhydride) copolymer ("PVE/MA") as a denture adhesive. This mixed partial salt may be a calcium salt combined with a monovalent sodium, potassium, or quaternary ammonium salt with the calcium to the monovalent cation ratio from 2:1 to 10:1 on a weight basis (on a mole ratio basis the ratio was stated to be from 1:1 to 5:1), with the polymer being from about 50–95% neutralized by the cations.

The PVM/MA Ca/Na salts disclosed in examples I–V of Germann are prepared by a semi-dry process in the presence of a small amount of water and isopropanol which is insufficient to completely dissolve all of the PVM/MA anhydride and hydrolyze all of the anhydride groups to the acid form. Consequently, the equivalents of acid available to completely neutralize all of the metal hydroxides charged in making a high calcium containing Ca/Na salt by the semi-dry process in Germann are often insufficient. The result being that the PVM/MA Ca/Na salt is actually a mixture of unreacted metal hydroxides, PVM/MA Ca/Na salt, and unreacted PVM/MA anhydride which has a distinct taste associated with it.

There have been many alternatives and improvements to the original Germann polymer salt. U.S. Pat. No. 5,395,867 (Prosise—assigned to ISP) uses calcium, sodium, strontium, zinc, magnesium and potassium cations to change the properties of the polymer salts. Prosise discloses a "wet process" which employs a stoichiometric excess of acid groups (90–96% water), thus assuring complete dissolution of the PVM/MA copolymer and complete hydrolysis of the anhydride groups in the PVM/MA copolymer to acid groups. Consequently, the wet process yields a Ca/Na PVM/MA salt which has better organoleptic properties than a dry or semi-dry process salt. Additionally, dental adhesive compositions produced by the wet process also show to have improved elastic properties.

One important factor in designing a denture adhesive salt is consumer acceptance of the organoleptic qualities of the salts in the denture adhesive. Another factor is the ease of manufacture of the adhesive salts. A major disadvantage of the wet process in the prior art to produce organoleptically acceptable denture adhesives is the tendency of the process to produce precipitates of PVM/MA Ca/Na salt, which is particularly a problem in manufacturing PVM/MA salts with a high degree of substitution in calcium (about 69% and greater). While this precipitated PVM/MA salt appears to have no activity as a denture adhesive salt, the salt precipitates when formed in large enough quantities in the salt-making reactors can plug reactor lines and pumps used to transfer the product to dryers causing expensive maintenance and down-time. Therefore, it is not possible to make dental adhesive compositions with a high degree of substitution because of plugging problems which basically stop the manufacturing process.

Prosise teaches that one of the copolymers from the copolymeric Ca/Na mixed salt are derived from is available as GANTREZ® AN, supplied by International Specialty Products (ISP, the assignee of the Prosise patent). Product literature from ISP/GAF Corporation (page 11, Gantrez® AN, technical bulletin 7543-017) discloses that the addition of calcium beyond 0.7 mol equivalents causes precipitation of Gantrez® AN. The problem can be avoided by not using more than 0.7 mol equivalents of calcium, i.e., avoiding the precipitation formed during further calcium neutralization "by replacement of calcium with caustic."

The inventor has surprisingly found that denture adhesive compositions can be manufactured comprising calcium/sodium PVM/MA salts formed via a wet process with the level of calcium beyond 0.7 mol equivalents. It is found that it is NOT necessary to avoid the precipitation, i.e., manufacturing problems by avoiding the addition of calcium beyond 0.7 mol equivalents. Contrary to the prior art teaching of "replacement of calcium with caustic," the addition of calcium well beyond the 0.7 mol equivalents (70% degree of substitution) is possible by controlling the amount of sodium and/or potassium hydroxide employed in producing calcium/sodium and/or potassium PVM/MA salts in the wet process.

There is also provided in the invention a denture adhesive paste comprising a mixed partial calcium/sodium or calcium/potassium salt of a PVM/MA wherein the degree of substitution of the copolymer in calcium is at least about 69%.

SUMMARY OF THE INVENTION

The invention provides a denture adhesive composition comprising a wet-process partial, mixed salt of a copolymer of an alkyl vinyl ether and maleic acid produced by a wet process, wherein the cations of said salt comprise: i) calcium with a degree of substitution of the copolymer in calcium is at least about 69%; and ii) at least one other cation selected from the group consisting of sodium and potassium.

In a preferred embodiment of the invention, the degree of substitution of the copolymer in calcium is in the range of about 69–80% and the degree of substitution of the other cation is about 1–10%.

The invention further provides a method for making denture adhesive compositions with a wet-process, partial, mixed salt of a copolymer of an alkyl vinyl ether and maleic acid, and wherein: the cations of the salt comprises: i) calcium with degree of substitution of the copolymer in calcium is at least about 69%; and ii) at least one other cation selected from the group consisting of sodium and potassium with a degree of substitution in the range of about 1–10%.

DESCRIPTION OF THE PREFERRED EMBODIMENTS

The principal object of the present invention therefore is to provide a denture adhesive comprising a salt of an alkyl vinyl ether/unsaturated anhydride or polycarboxylic acid copolymer with acceptable organoleptic properties and good processing properties.

The denture adhesive compositions of the present invention can be formulated in liquid, cream, liner, and possibly powder forms that, when in contact with saliva, develop a high degree of tack and uniform viscous mucilages of high cohesive strength and that, when spread over the denture-mucosa interface, provide superior denture stabilizing properties. The compositions contain a denture adhesive salt together with excipients.

Denture Adhesive Salt

The denture adhesive employed in the composition is a partial salt of a copolymer of maleic acid and an alkyl vinyl ether (collectively referred to as "PVM/MA"). Preferably, the alkyl group has from about 1 to about 5 carbon atoms, but a more preferable copolymer includes methyl vinyl ether. As is known by those skilled in the art, the molecular weight of such copolymers can affect the properties of the copolymer and, by extension, the denture adhesive comprising the copolymer. Polymers generally do not have one precise molecular weight. Rather, polymers are made up of many polymer molecules, each having a different molecular weight. One way to measure the "average" molecular weight of a polymer is to measure its specific viscosity under specified conditions. The preferred copolymer of the invention generally has a specific viscosity (measured as a 1% weight/volume solution of methyl ethyl ketone at 25° C.) of at least about 1.5. More preferably, the specific viscosity is at least about 2.5.

The preferred copolymer of the invention is generally used as its partial salt. The maleic anhydride group can be hydrolyzed to form the corresponding dicarboxylic acid which can, in turn, react with metal compounds that partially neutralize the carboxylic acid groups on the copolymer.

Preferably less than 100% of the carboxylic acid groups on the copolymer chain are neutralized. More preferably, about 26% to about 15% of the carboxylic acid groups are left unneutralized of the copolymer and most preferably from about 24% to about 15% of the carboxylic acid groups.

One of the cations in accordance with the invention is calcium. Another cation in accordance with the invention is an alkali metal cation, preferably sodium and/or potassium.

As indicated before, it has been suggested in the prior art that the addition of the cation calcium beyond 70% degree of substitution causes precipitation of the PVM/MA copolymer, thus making it impossible to manufacture the Ca/Na salt composition. It has also been suggested that the calcium be replaced by caustic. Instead of replacing calcium with sodium and/or potassium as suggested in the prior art, it has been surprisingly found that the problematic Ca/Na PVM/MA salt precipitate formation can be eliminated even with high levels of calcium substitution (69% or greater) by holding the substitution level of the other cation, i.e., sodium and/or potassium within certain limits.

The substitution level of the other cation is preferably kept at a decreasing level with increasing level of substitution of calcium. More preferably, the substitution level of the other cation is kept within the range of about 1 to 10%. Most preferably, the substitution level of the other cation is kept approximately within the following range with respect to the degree of substution in calcium:

TABLE 1

Most preferred embodiment - degree of substitution of Ca:Na

| Degree of substitution - Ca | Degree of substitution - Na |
|---|---|
| 69% | 1-10% |
| 71% | 2-8% |
| 73% | 2.5-8% |
| 75% | 3-6% |
| 77% | 4-5.5% |
| 80% | 4.5-5.5% |

Other Ingredients

The dental adhesive compositions of the present invention may further comprise a water-soluble cellulosic polymer as is known in the art such as methyl cellulose, sodium carboxymethyl cellulose, hydroxyl propyl methyl cellulose and the like. The cellulosic polymer, preferably sodium carboxymethyl cellulose, is a powder which when moistened, becomes hydrated and tacky or gummy thereby providing additional adhesive functionality to the dental adhesive composition. The sodium carboxymethyl cellulose gums are water-soluble, anionic long chain polymers whose properties vary to some extent depending on the number of carboxymethyl groups that are substituted per anhydroglucose unit in each cellulose molecule. These cellulose polymers comprise from about 15% to about 35%, and preferably from about 17% to about 28% of the dental adhesive composition.

The denture adhesive may also comprise an activator such as a polyacrylic acid, polycarbophil, citric acid, sodium or calcium citrate and/or a polymeric acid such as a Gantrez® acid. Preferably, the activator comprises a polymer, such as relatively short chain resins and longer polymers, copolymers, graft or block copolymers, and linears or network polymers. Such materials can be naturally-occurring or derived or entirely artificial. Preferred materials include chelating polymeric acids and salts. Preferred chelating acids and salts comprise copolymers of dicarboxylic materials such as methyl-vinyl ether/maleic acid copolymers and acrylic acid/maleic acid copolymers.

Preferably, the lower alkyl vinyl ether-maleic acid is present in an amount of about 0.1% to about 1.5% by weight based on the total weight of the denture adhesive composition. More preferably, the lower alkyl vinyl ether-maleic acid is present in an amount of about 1% by weight based on the total weight of the denture adhesive composition.

Excipients

Typical excipients include waxes and oils. Other excipients often included in denture adhesives include flavoring agents, sweetening agents, viscosity modifiers, coloring agents, preservatives and thickeners. Other water soluble polymers such as xanthan gum, polyvinyl pyrrolidone (PVP), carboxymethyl cellulose, methyl cellulose and hydroxyl propyl guar may also form part of the final denture adhesive formulation. Vehicles such as petrolatum, mineral oil, vegetable oil and the like may form part of cream-type formulations, and non-toxic anti-caking agents such as silica, talc, dicalcium phosphate anhydrous and the like can be present. The compositions can also contain, if desired, other known denture adhesives.

The oils useful in the invention include without limitation is mineral oil. However, vegetable oils such as corn, soybean, cottonseed, castor, palm and coconut oils and animal oil such as fish oil may also be used in addition to mineral oil. In general, amounts of oil from about 1% to about 30% by weight of the total denture adhesive composition are usable, with amounts of about 10% to about 25% being preferred.

The colorants useful in the present invention include pigments such as titanium dioxide, and may also include the lakes of dyes suitable for food, drug and cosmetic applications. These colorants are known as D&C dyes. Two preferred colorants are the lakes of D&C Red No. 7 and D&C Red No. 30.

Fumed silica can also be used as a thickener for the adhesive. A fine white powder, fumed silica is the colloidal form of silica (silicon dioxide, $SiO_2$) made by the combustion of silicon tetra-chloride in a hydrogen-oxygen furnace. The amount of fumed silica used in the composition may range from about 0.7% to about 2%.

Preparation

The denture adhesive composition of the invention can be prepared by mixing the components until a homogeneous mixture and is obtained and recovering the resulting product. For example, if polyethylene and mineral oil are to be employed, such material may be heated to temperatures from about 90 to 95° C., and are preferably cooled prior to blending with other components such as the polymeric acid and coloring agents.

Whether formulated as a powder, liner, liquid or cream, the denture adhesive composition of the present invention hydrates to form an adhesive composition when applied to moist dentures or exposed to water or saliva.

In order to further illustrate the present invention, various illustrative examples are set forth below. In these examples, as well as throughout the specification and claims, all parts and percentages are by weight and all temperatures in degrees Celsius unless otherwise specified.

EXAMPLES 1–2

Polymer salts were prepared in the following manner. 900 g of room temperature water were charged into a main reactor kettle equipped with a high speed stirrer. The anhydrous MVE/MA copolymer was slowly added to the main mix kettle with continuous mixing. 250 g of room temperature water were charged into a secondary kettle and either sodium hydroxide or potassium hydroxide and calcium hydroxide were added slowly. This slurry was well mixed to form a homogenous slurry. The slurry was slowly added into the main reactor kettle while mixing at high speed to prevent localized precipitation. The batch was heated to 85° C. (±5° C.) and maintained at about 85° C. for two hours with vigorous mixing, forming the salt. These salts remained in solution and did not precipitate or settle thus ruining the batch. The resulting mixture was put in trays and dried at 85° C. in an oven or dried on a drum drier.

The dried Ca/Na, or Ca/K 75/5, 80% degree of substitution salt was then milled through a suitable mill and screened through a 60 mesh screen. A one percent solution of the resulting powder had a pH of about 5.5–6.5 and a bulk density of 0.7–0.8. The materials used and the amounts used are set forth in Table 2. These salts did not precipitate or settle.

TABLE 2

Formulation of Examples 1 and 2

| Ingredient | Example 1 | Example 2 |
|---|---|---|
| Water | 1150 g | 1150 g |
| GANTREZ ® AN169 | 72.38 g | 72.79 g |
| Calcium hydroxide | 25.77 g | 25.90 g |
| Sodium hydroxide | 1.82 g | — |
| Potassium hydroxide | — | 2.6 g |

COMPARATIVE EXAMPLE

A polymer was made according to example 1, except that an amount of sodium hydroxide was employed that was sufficient to form a Ca/Na 75/8, 83% degree of substitution salt. After the mixer was turned off, a heavy deposit of precipitate was observed on the bottom of the glass reactor and the batch had to be discarded.

The purpose of the above description is to illustrate some embodiments of the present invention without implying a limitation. It will be apparent to those skilled in the art that various modifications and variations may be made in the apparatus or procedure of the invention without departing from the scope or spirit of the invention.

What is claimed is:

1. A denture adhesive composition consisting essentially of a partial, mixed salt of an alkyl vinyl ether and maleic acid copolymer wherein a stochiometric excess of acid groups remains after salt formation is complete, and wherein the cations of said salt comprise:

a) calcium with a degree of substitution of the copolymer in calcium about 71% or higher; and b) at least one other cation selected from the group consisting of sodium and potassium; and wherein the degree of substitution of said copolymer in said at least one other cation is greater than about 2% and less than about 10%.

2. The denture adhesive composition of claim 1, wherein the degree of substitution of the copolymer in calcium is in the range of about 69–80%.

3. The denture adhesive composition of claim 1, wherein the degree of substitution of said copolymer in said at least one other cation is in the range of about 1–10%.

4. The denture adhesive composition of claim 1, wherein the degree of substitution of the copolymer in calcium relative to the degree of substitution of said copolymer in said at least one other cation is defined in the following relationship:

about 1–10% degree of substitution of said copolymer in said at least one other cation for 69% degree of substitution of said copolymer in Ca;

about 2–8% degree of substitution of said copolymer in said at least one other cation for 71% degree of substitution of said copolymer in Ca;

about 2.5–8% substitution of said copolymer in said at least one other cation for 73% degree of substitution of said copolymer in Ca;

about 3–6% degree of substitution in said at least one other cation for 75% degree of substitution of said copolymer in Ca;

about 4–5.5% degree of substitution in said at least one other cation for 77% degree of substitution of said copolymer in Ca; and about 4.5–5.5% degree of substitution in said at least one other cation for 80% degree of substitution of said copolymer in Ca.

5. The denture adhesive composition of claim 1, formulated into a powder adhesive.

6. The denture adhesive composition of claim 1, formulated into a denture adhesive liner.

7. The denture adhesive composition of claim 1, formulated into a liquid adhesive.

8. The denture adhesive composition of claim 1, wherein the copolymer is a methyl-vinyl ether and maleic acid copolymer.

9. A method for making denture adhesive compositions comprising:

a) mixing a copolymer of an alkyl vinyl ether and maleic acid with water, calcium hydroxide and at least one of sodium hydroxide and potassium hydroxide under wet-process reacting conditions to form a partial, mixed salt of the copolymer materials, and wherein the cations of the salt comprise: i) calcium with a degree of substitution of the copolymer in calcium is at least about 69%; and ii) at least one other cation selected from the group consisting of sodium and potassium with a degree of substitution in said at least one other cation in the range of about 1–10%; and b) drying said salt to form a powder;

c) mixing the powder with at least one or more excipients to form a denture adhesive composition.

10. The method of claim 9, wherein the degree of substitution of the copolymer in calcium is in the range of about 69–80%.

11. The method of claim 9, wherein the degree of substitution of the copolymer in said at least one other cation decreases with increasing degree of substitution of the copolymer in said calcium.

12. The method of claim 9, wherein the degree of substitution of said copolymer in said said at least one other cation relative to the degree of substitution of the copolymer in said calcium is defined in the following relationship:

about 1–10% degree of substitution of said copolymer in said at least one other cation for 69% degree of substitution in Ca;

about 2–8% degree of substitution of said copolymer in said at least one other cation for 71% degree of substitution in Ca;

about 2.5–8% degree of substitution of said copolymer in said at least one other cation for 73% degree of substitution in Ca;

about 3–6% degree of substitution of said copolymer in said at least one other cation for 75% degree of substitution in Ca;

about 4–5.5% degree of substitution of said copolymer in said at least one other cation for 77% degree of substitution in Ca; and about 4.5–5.5% degree of substitution of said copolymer in said at least one other cation for 80% degree of substitution in Ca.

* * * * *